(12) United States Patent
Mathew et al.

(10) Patent No.: US 7,955,264 B2
(45) Date of Patent: Jun. 7, 2011

(54) SYSTEM AND METHOD FOR PROVIDING COMMUNICATION BETWEEN ULTRASOUND SCANNERS

(75) Inventors: Prakash Parayil Mathew, Mukwonago, WI (US); Sastry V. S. Chilukuri, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 1083 days.

(21) Appl. No.: 10/885,870

(22) Filed: Jul. 7, 2004

(65) Prior Publication Data

US 2006/0009695 A1 Jan. 12, 2006

(51) Int. Cl.
*A61B 8/00* (2006.01)
(52) U.S. Cl. ............ 600/447; 600/407; 600/437
(58) Field of Classification Search .......... 600/443, 600/447
See application file for complete search history.

(56) References Cited

U.S. PATENT DOCUMENTS

| | | | | |
|---|---|---|---|---|
| 5,487,172 A | * | 1/1996 | Hyatt | 712/32 |
| 5,492,125 A | * | 2/1996 | Kim et al. | 600/443 |
| 5,787,889 A | * | 8/1998 | Edwards et al. | 600/443 |
| 5,853,367 A | * | 12/1998 | Chalek et al. | 600/437 |
| 5,935,070 A | | 8/1999 | Dolazza et al. | |
| 5,963,212 A | | 10/1999 | Bakalash | |
| 6,171,244 B1 | * | 1/2001 | Finger et al. | 600/437 |
| 6,350,239 B1 | * | 2/2002 | Ohad et al. | 600/437 |
| 6,440,071 B1 | * | 8/2002 | Slayton et al. | 600/437 |
| 6,526,163 B1 | * | 2/2003 | Halmann et al. | 382/128 |
| 6,578,002 B1 | * | 6/2003 | Derzay et al. | 705/2 |
| 6,683,933 B2 | | 1/2004 | Saito et al. | |
| 6,753,873 B2 | | 6/2004 | Dixon et al. | |
| 7,016,719 B2 | * | 3/2006 | Rudy et al. | 600/513 |
| 2002/0007119 A1 | * | 1/2002 | Pelissier | 600/443 |
| 2003/0115018 A1 | * | 6/2003 | Sharma et al. | 702/183 |
| 2005/0148878 A1 | * | 7/2005 | Phelps et al. | 600/459 |

FOREIGN PATENT DOCUMENTS

| | | |
|---|---|---|
| JP | 02283358 | 11/1990 |
| JP | 03016560 | 1/1991 |
| JP | 04319340 | 11/1992 |
| JP | 05188138 | 7/1993 |
| JP | 09081021 | 3/1997 |
| JP | 200125888 | 9/2001 |
| JP | 2002336241 | 11/2002 |
| JP | 2002360570 | 12/2002 |
| JP | 2003233674 | 8/2003 |
| JP | 2004120094 | 4/2004 |
| WO | 9933400 | 7/1999 |
| WO | 03094712 | 11/2003 |

* cited by examiner

*Primary Examiner* — Brian Casler
*Assistant Examiner* — Jonathan G Cwern
(74) *Attorney, Agent, or Firm* — Dean Small; The Small Patent Law Group

(57) ABSTRACT

System and method for ganged ultrasound scanners is described. The described system includes a plurality of ultrasound scanners configured as a network and at least one connector for connecting a single ultrasound probe to the plurality of ultrasound scanners. The connector is configured to provide communication between the plurality of ultrasound scanners and the ultrasound probe.

21 Claims, 6 Drawing Sheets

SYSTEM AND METHOD FOR PROVIDING COMMUNICATION BETWEEN ULTRASOUND SCANNERS

BACKGROUND OF THE INVENTION

This invention relates generally to medical imaging systems, and more particularly, to providing communication between ultrasound scanners in a medical imaging system.

Medical imaging systems are requiring more computational power and memory to perform scans providing higher quality images. Particularly in ultrasound diagnostic medical imaging, the imaging processes are requiring higher computational processing power. The processes require more CPU, memory and storage capacity to perform the image processing required in ultrasound imaging. Improved image quality require larger data sizes to be processed. Moreover, output displayed as three dimensional (3D) and time varying 3D images (known as 4D images) also require larger amounts of raw data and additional processing power to process this more complex raw data.

To provide improved quality images, probes or other medical examination devices must be configured to acquire larger sizes of data. Such probes typically will require a greater number of channels. Often the channels are processed in parallel to acquire a better image quality or decrease scan time.

Improving image quality will require increased computational power of medical imaging scanners. However, this will require modifying existing scanner, replacing existing scanners or performing scans in steps if the processing power of the scanner is insufficient to process the data in a single process.

BRIEF DESCRIPTION OF THE INVENTION

In one exemplary embodiment, an ultrasound system is provided that includes a plurality of ultrasound scanners configured as a network and at least one connector for connecting a single ultrasound probe to the plurality of ultrasound scanners. The connector is configured to provide communication between the plurality of ultrasound scanners and the ultrasound probe.

In another exemplary embodiment, a method for controlling operation of an ultrasound probe is provided. The method includes configuring a plurality of ultrasound scanners for communication to control a single ultrasound probe and controlling the operation of the ultrasound probe with the plurality of ultrasound scanners.

DETAILED DESCRIPTION OF THE INVENTION

Various embodiments of the invention provide a system and method for combining medical imaging devices. The embodiments utilize parallelism in an application flow where the application requires high computational resources. Multiple channels of data flow into the system via a transducer element, with different portions of the multiple channels of data processed by different scanners.

Figure 1:
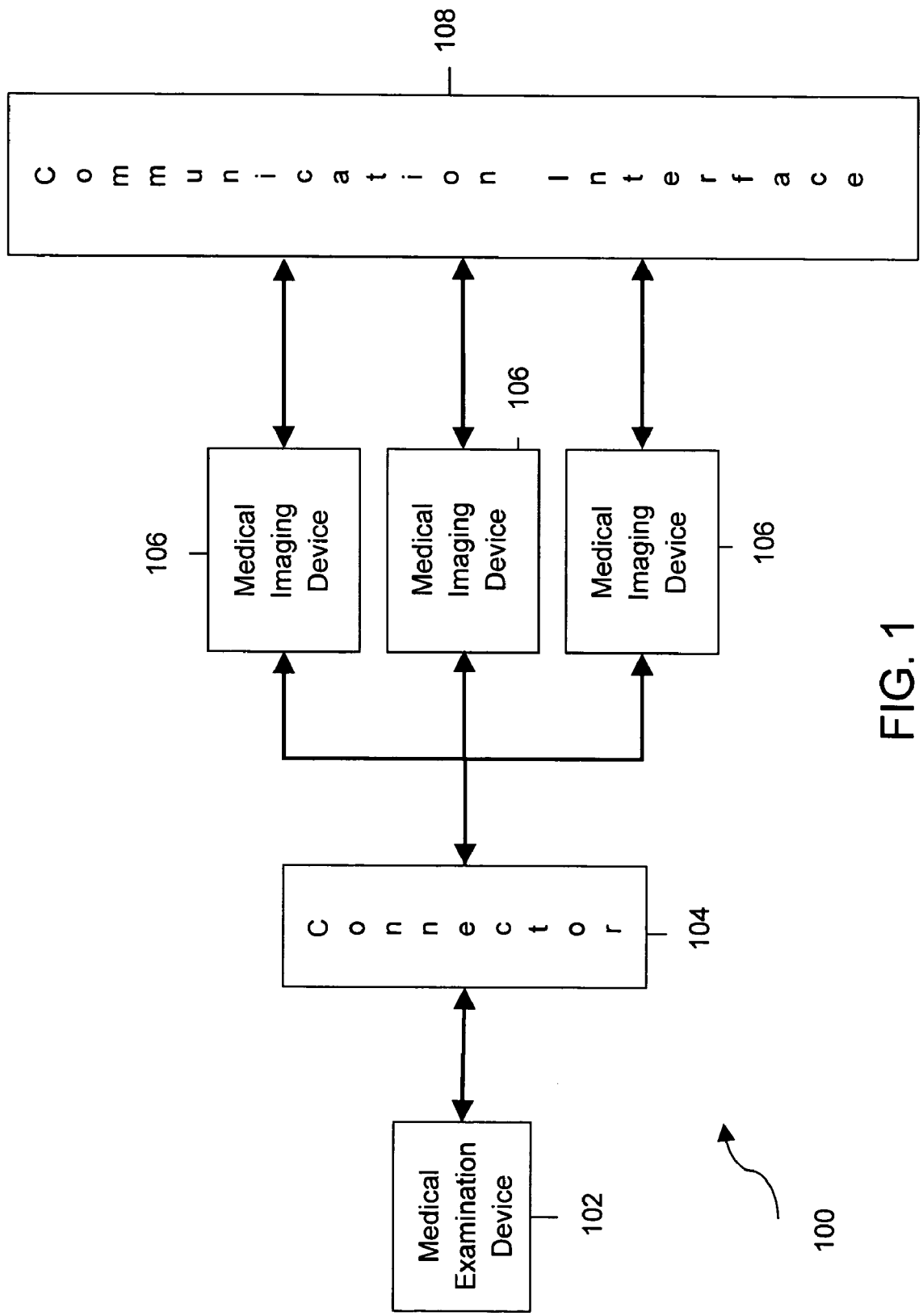
FIG. 1 is a block diagram of a medical imaging system in accordance with an exemplary embodiment of the invention.

Specifically, FIG. 1 is a block diagram of a medical imaging system in accordance with an exemplary embodiment of the invention. Medical imaging system 100 includes a medical examination device 102 to collect raw input data. The data can be data such as, for example, echoes from an ultrasound probe or data for an electrocardiograph (ECG). Medical examination device 102 may be any medical examination device such as, for example, an ultrasound probe or an electroencephalogram (EEG) needle. Medical examination device 102 is connected via a connector 104 to a plurality of medical imaging devices 106. Connector 104, in various embodiments is configured to provide an interface to connect one medical examination device 102 to the plurality of medical imaging devices 106. Connector 104, in various embodiments, also may be configured to divide the data from medical examination device 102 among the various medical imaging devices 106. It should be noted that the plurality of medical imaging devices (e.g., ultrasound scanners) may be of the same or different type and have the same or different processing, communication and control characteristics.

In operation, acquired data is communicated to medical imaging devices 106 via connector 104. The data may be processed by medical imaging devices 106 to generate an image. Medical imaging devices 106 are configured in a ganged arrangement to combine, for example, the processing and/or computational power of each of the medical imaging devices 106. Each medical imaging device 106 processes part of the acquired data received by the medical imaging device 106 and as described in more detail herein. The data is processed, for example, using imaging applications or algorithms stored in the medical imaging devices 106. Each medical imaging device 106 thereby may generate a partial result. The partial results may be, for example, scan converted data that is communicated over a communication interface 108 and then reversed or combined. The merged or combined results then, for example, may be provided to a display for displaying or may be further processed as desired or needed (e.g., enhance the image).

To communicate the partial results as well as information such as control signals, medical imaging devices 106 communicate through communication interface 108. In one embodiment of the invention communication interface 108 is part of a communication network, such as, for example, an Ethernet or a Fiber-Channel network, which may be a wired or wireless network. The communication network is discussed in more detail in connection with FIG. 4. Various other networks may be implemented, for example, based on the communication requirements of the medical imaging devices 106

Figure 2:
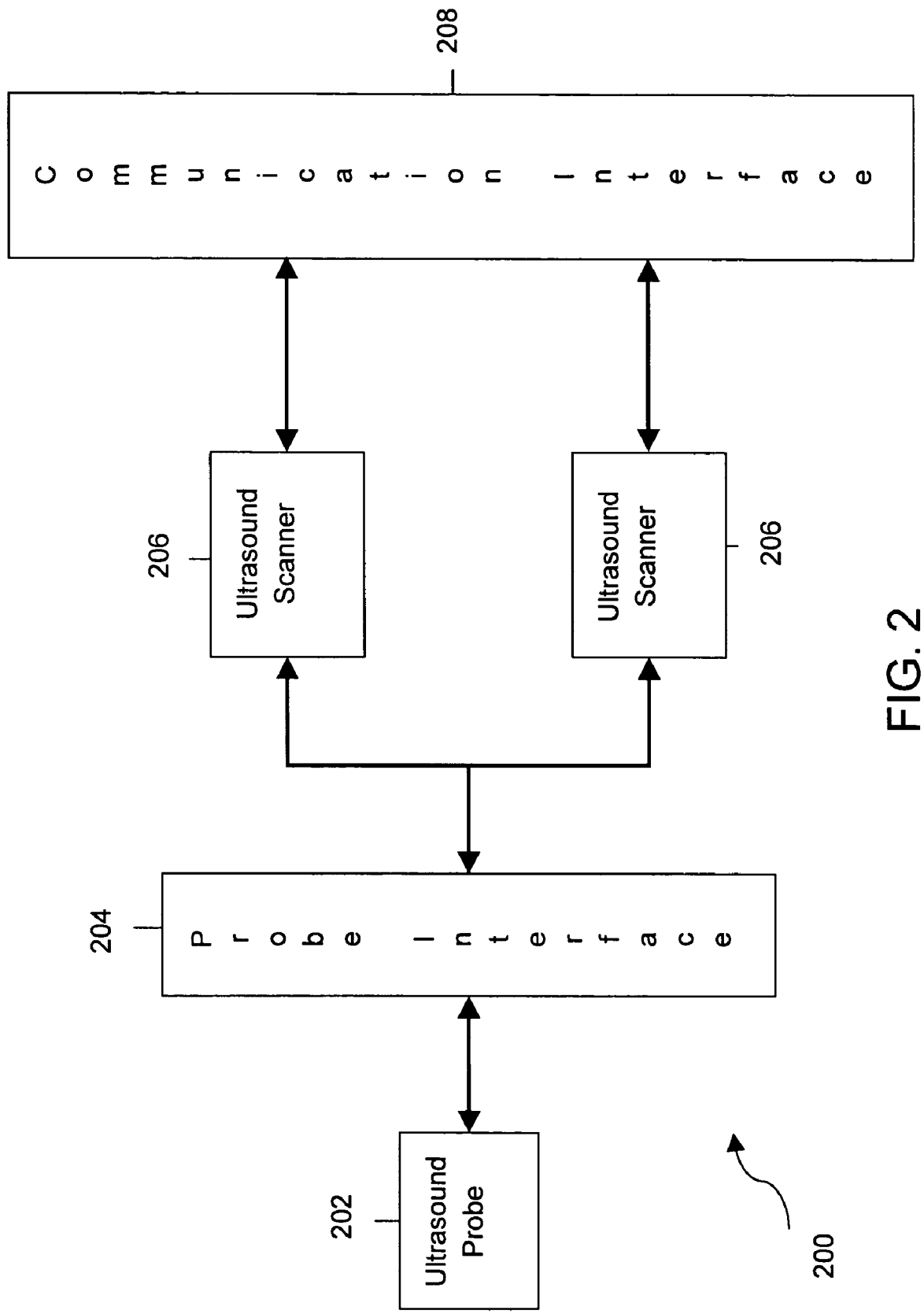
FIG. 2 is a block diagram of an ultrasound system in accordance with an exemplary embodiment of the invention.

FIG. 2 is a block diagram of an ultrasound system 200 in accordance with an exemplary embodiment of the invention. The ultrasound 200 includes a system probe 202 for acquiring input data. For example, the probe 202 may be an ultrasound probe configured to receive echoes from a body in a predetermined frequency range. For elevational focusing, image quality or other requirements, a high capacity probe, such as, for example, a 512-channel probe may be used. All the channels of probe 202 may need to be processed simultaneously, thus requiring 512 inputs to the ultrasound system 200. The probe 202 may have any number of channels, such as, for example, 128, 256, 512, 1024 and 2048. Also, the probe 202 may be any type of probe, such as, for example, a linear probe, a 2D matrix probe or a curvilinear array probe.

In operation probe 202 transmits an ultrasound signal and receives the echoes. Multiple beams are simultaneously transmitted and received for obtaining the data for ultrasound scanners 206. The use of simultaneous transmitted beams is known as Multi Line Transmit (MLT). The required separation between the simultaneously transmitted beams is maintained either spatially or through the use of codes. The use of codes for the separation is called Coded Excitation as is known. The excitation signal generated for transmission of a beam is provided along with a code. This code is used by a transmitter to identify the signal communicated to the transmitter. The transmitter ignores any other signal and accepts only these signals. In accordance with other embodiments of the invention, collected input data is received using Multi Line Acquisition (MLA).

The acquired data, for example, echoes, form the collected input data. The collected data is communicated to ultrasound scanners 206 via a probe interface, which in various embodiments is configured as a connector 204. Connector 204 splits the signal received from ultrasound probe 202 and provides a part of the split signal to each of the ultrasound scanners 206. Connector 204 is described in more detail in connection with FIG. 3.

In accordance with an exemplary embodiment of the invention, each of the ultrasound scanners 206 support a plurality of channels for data processing, such as, for example, 128, 256 or 512 channels. Each ultrasound scanner 206 is provided only part or a portion of the data such that the scanners 206 process only that portion of the data.

Ultrasound scanners 206 are connected to imaging system 200 and to each other via communication interface 208. Communication interface 208 provides transmission of information such as, for example, raw data, processed data, results and control signals. In one embodiment of the invention, communication interface 208 includes more than one communication network. These communication networks may be high speed or low speed, wired or wireless networks. Further, although only two ultrasound scanners 206 are shown, additional ultrasound scanners 206 may be interconnected.

In operation, one of the plurality of scanners 206 is selected and configured as a 'master' scanner. In one embodiment, the user controls of only the master scanner are operational and available to a user. Further, the images resulting from processing the data are also only displayed on the display associated with the master scanner in this embodiment. The other scanners 206 are configured as 'slaves'. In various embodiments of the invention, different combinations and numbers of scanners 206 may be provided. In such instances, only one scanner is configured as a master scanner and the remaining are configured as slave scanners being controlled by the master scanner 206. In accordance with an embodiment of the invention, the master scanner 206 determines the number of scanners required for processing the data based on the number of channels provided on utilized probe 202 and accessed and/or connects/communicates with only those scanner 206 needed.

Software residing on a backend processor, (e.g., computer), of each scanner 206 allows the scanner to be configured as a master or as a slave as is known. By configuring the processors of the scanners 206, the scanners 206 can be configured into the necessary master-slave modes. The master scanner 206 will receive information regarding each of the slave scanners 206, such as, for example, the IP addresses of the slave scanners 206. The master scanner 206 further ensures that there is no conflict, such as, for example, two master scanners 206 among the scanners 206. Such conflicts may be resolved based on user configuration.

Each scanner 206 (including the master scanner 206) operates and controls only a partial number of the channels available on probe 202. Thus, each scanner 206 receives only part of the collected input data from the channels the scanner 206 is controlling. For example, if the ultrasound probe 202 is a 512-channel probe, and two scanners 206 are present, the master scanner 206 controls channels 1-256 of probe 202 and the slave scanner 206 controls channels 257-512 of probe 202, or vice versa.

In one embodiment, the frontend signal transmission and processing of data is performed in parallel by all the scanners 206. Thus, the capability of each scanner 206, such as the beam parameter computation, scan sequencing, transmitting, receiving, analog/digital conversion and beam-forming EQ filtering, Bitmap (BMP) processing and scan control bus functionality is available to control the probe 202. Each scanner 206 generates a partial result based on the data the scanner 206 acquires or receives. For example, the resultant B-M Mode vector data or IQ (for Color Doppler) from each scanner 206 that has been processed or scan converted, represents the partial results. For a combined scan, all the partial results are merged or combined to obtain, for example, an aggregate image (e.g., high quality image). In various embodiments of the invention, the master scanner 206 merges or combines the partial results into one complete image. However, the partial results may be merged at other locations, for example, at a slave scanner 206 or a dedicated processing machine.

Figure 3:
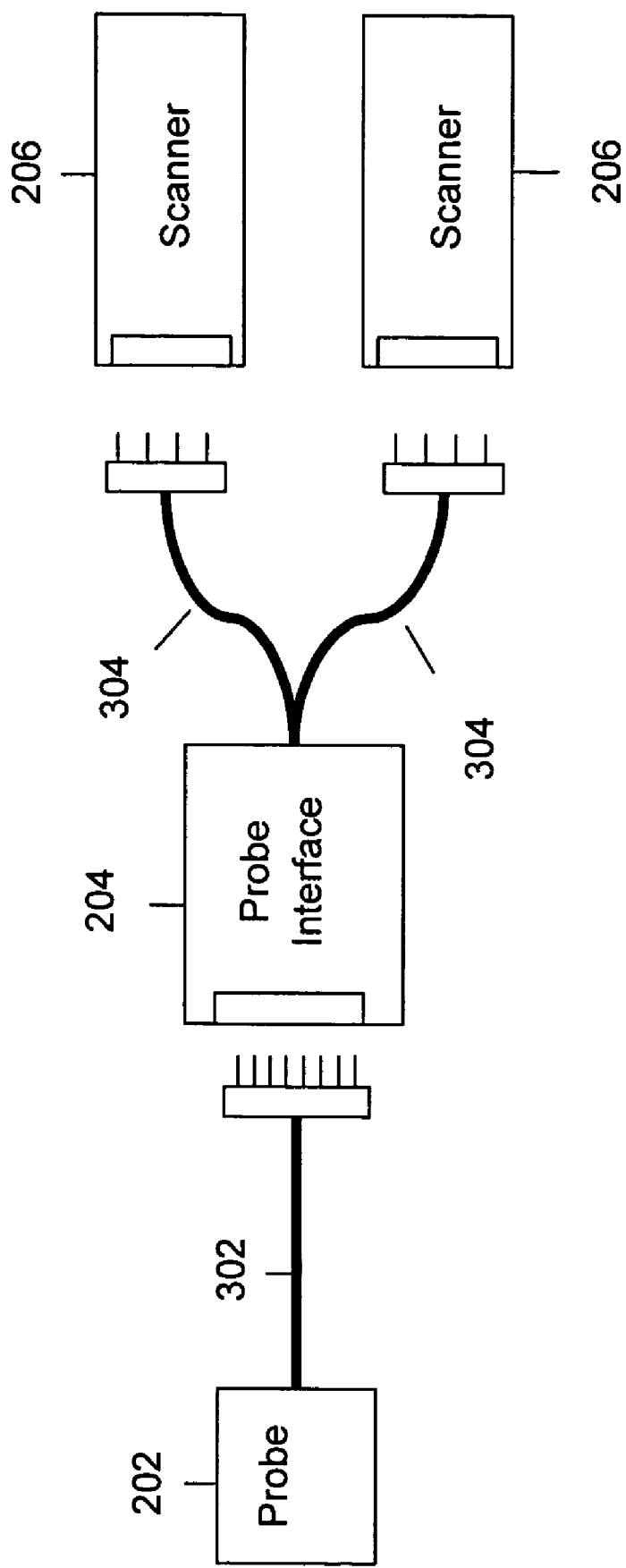
FIG. 3 is a block diagram showing a connector in accordance with an exemplary embodiment of the invention.

FIG. 3 is a block diagram showing the probe interface configured as a connector 204 in accordance with an exemplary embodiment of the invention. Connector 204 connects and/or interfaces one probe 202 with a plurality of output channels, such as ultrasound probe 202 with 512-channels, to more than one scanner 206 each have a lesser number of channels, such as two ultrasound scanners 206 each with 256-channels. Therefore, the connector 204 splits the 512-channels to two sets of 256-channels. However, it should be noted that the connector 204 may be configured to split the channels into different sizes of sets of channels (e.g., four sets of 128 channels).

For example, each ultrasound scanner 206 may include a 256-channel female connector, with ultrasound probe 202 having a 512-channel male connector. Connector 204 is then configured having a 512-channel female connector and two 256-channel male connectors, such that the connectors of connector 204 fit into connectors of probe 202 and scanners 206, respectively.

Cables 302 and 304 (e.g., flexible cables) are provided to connect ultrasound probe 202 to ultrasound scanners 206. Cables 304 form two legs of connector 204 and in one embodiment are equal in length. The equal length of cables 304 equalizes the propagation distance of each ultrasound pulse received as well as transmitted along the two legs. Cables 304 are configured to such a length as to reach the connector ports on ultrasound scanners 206. It should be noted that cables 302 and 304 may include a plurality of wires or cables. In accordance with an exemplary embodiment of the invention, the number of the cables is reduced using Capacitive Micromachined Ultrasound Technology (CMUT technology).

In an exemplary embodiment of the invention, an indicator such as a Light Emitting Diode (LED) may be provided to indicate the state of the electromechanical connection. The power for driving these LEDs is derived from one of the ultrasound scanners 206 and may be provided through a dedicated line in the cable bundle.

Input data is provided to scanners 206 via connector 204 through cables 302 and 304. However, other means of communication may be provided for communicating partial results as described below. Also, the slave scanners 206 receive user command inputs for a user through the user controls of the master scanner 206 as described below.

Figure 4:
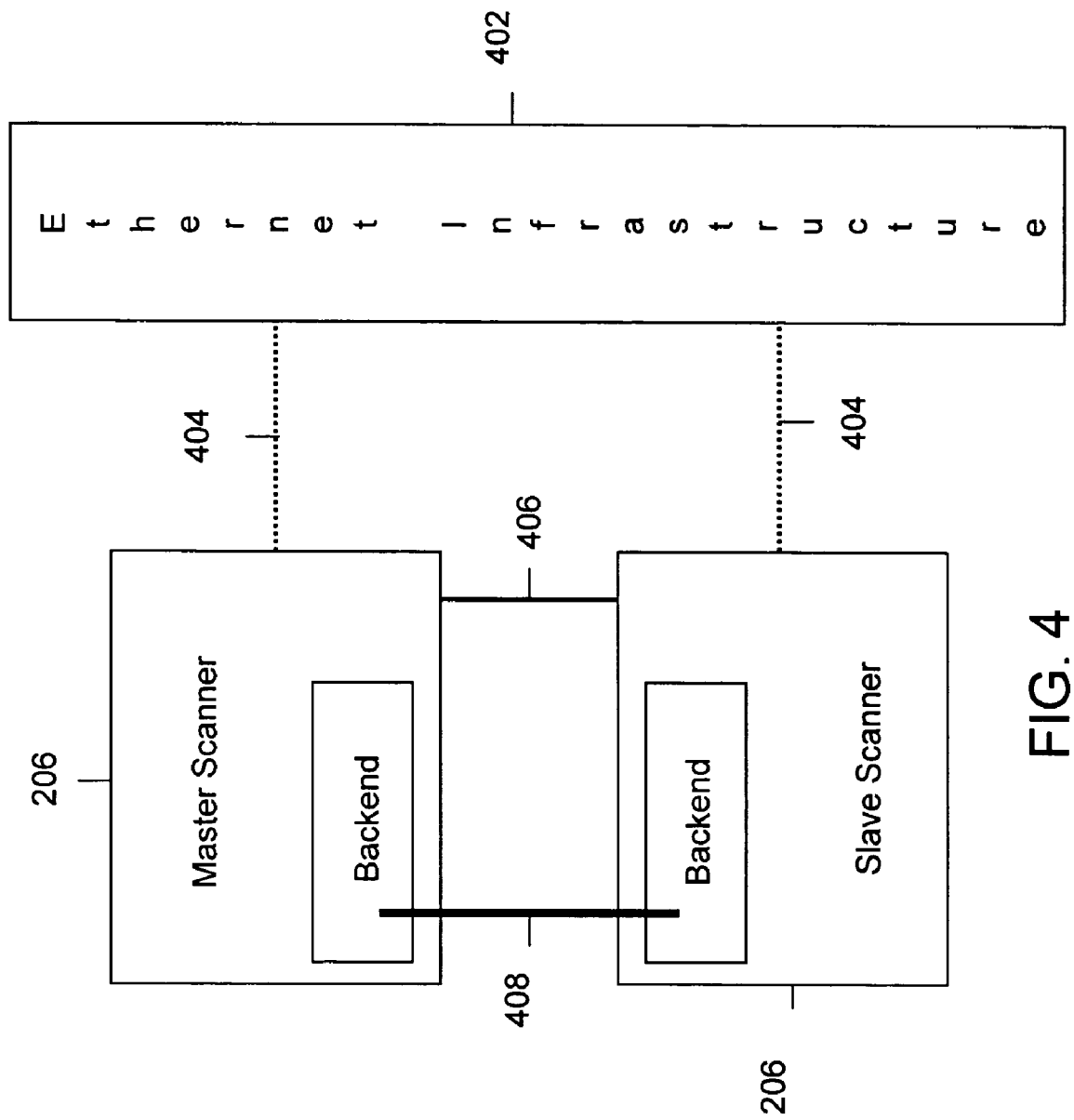
FIG. 4 is a block diagram of communication interfaces in accordance with an exemplary embodiment of the invention.

FIG. 4 is a block diagram of the communication interfaces in accordance with an exemplary embodiment of the invention. The scanners 206 that are connected (e.g., in ganged communication) to ultrasound probe 202 (shown in FIG. 2) are configured to communicate with each other. Two types of communication networks are provided. One is a communication network, wherein communication time is not critical and the other is a high speed communication network wherein communication time is critical (e.g., for synchronous operation of parallel control of elements of ultrasound probe 202).

In operation, any user may change controls such as, for example, gain. In one embodiment, the changes are input via user controls of the master scanner 206 (e.g., GUI). The user inputs (e.g., changes) are communicated to the slave scanners 206. Such user commands communicated to the slave scanners 206 are typically not time critical and, hence, are not communicated over a high speed link. Moreover, such link may have a low bandwidth as setup data such as probe setup relating to ultrasound beam-forming parameters and geometry can be pre-loaded into the system or these parameters can be computed in real time by each unit. This communication is generally designed to be via an Ethernet link using, for example, Transmission Control Protocol/Internet Protocol (TCP/IP). Scanners 206 may be part of a site network, such as, for example, a hospital network. A network of the scanners 206 then may be configured as a virtual subgroup over the infrastructure of the site network. In accordance with various embodiments of the invention, an Ethernet infrastructure 402 provides this communication. Control signals, such as, for example, probe or mode configuration changes, application changes, in general, other real time user actions or inputs are communicated to the slave scanners using the Ethernet infrastructure 402. The Ethernet link also communicates data traffic to maintain the state of scanners 206. The state of scanners 206 is also continuously monitored and alarms are checked using the Ethernet infrastructure 402. The alarms checked may be alarms such as, for example, scanners 206 power off, power reset, beamformer frontend reset, temperature fault conditions, communication link down and connector fault.

Scanners 206 are connected to Ethernet infrastructure 402 through a connection 404. Connection 404 may be, for example, wired or wireless. For example, connection 404 may be wireless to communicate through walls or over distances where cables are not available. In accordance with various embodiments of the invention, a secondary network cable 406 is connected to each of the scanners 206 via, for example, a Network Interface Card (NIC) card and a hub. For example, secondary network cable 406 may be a Category-5 (according to International Standards Organization standards) cable (CAT-5 cable).

The transmission of the user commands is not bandwidth intensive and is thus communicated over Ethernet infrastructure 402 and via network cables 406. The transmission of result data is more time and bandwidth intensive. For example, for 1024 frames and 512 points per frame, about 2 MB of data for a B-mode frame is produced. At 60 frames per second (fps), about 120 MB/s of data is produced. Thus, a transfer rate of about 60 MB/s from each slave scanner 206 may be needed. A standard or proprietary interface 408 is provided between the master scanner 206 and each slave scanner 206 capable of transferring at the needed transfer rate, for example, at least 60 MB/s.

Propriety or standard interface 408 in one embodiment, includes high speed serial links that are configured as data aggregation links. The propriety or standard high speed serial links are synchronous high speed links with a typical data transfer rate of at least 60 MB/s. The links may be provided as mechanically flexible and deployable cables for connection between scanners 206.

In one embodiment, propriety or standard interface 408 is a Gigabit Ethernet (GigE). The GigE link that is used to maintain the master-slave configuration is also used to communicate partial results to the master scanner 206. GigE may be physically implemented over, for example, optic fiber with electro optical transceivers on the scanner backend. The GigE provides full duplex data rates of up to 70 MB/s. For lower frame rates, the Ethernet connection 404 used to connect the scanners 206 to the site communication infrastructure such as the Ethernet infrastructure 402 is used. A dedicated secondary GigE connection also may be provided using another NIC card on each scanner 206. To provide TCP/IP processing, each scanner 206 may use a TCP Offload Engine (TOE) that includes dedicated CPU cards to pack and reform TCP packets. Using Remote Direct Memory Access, data is read out of the Direct Memory Access (DMA) frame buffers at each end directly into dual ported memory at the slave end.

Once data has been communicated to a master backend processor, the data is processed to form the final aggregated image (e.g., high resolution/quality image). The backend processor of the master scanner 206 may be a high capacity processor. In accordance with various embodiments of the invention, a dual CPU architecture is used in the master processor backend. In this backend, the scan converted data from each of the slave scanners 206 (and the master scanner 206) is processed. The processing may include extrapolation of the data and processing this into pixel space. The pixel space is the space in which the final image may be represented. The image then may be displayed on a display of the master scanner 206. In other various embodiments of the invention, a single high capacity CPU may be used at the backend of the master scanner 206.

In various embodiments, the final displayed image is generated by merging and processing individual partial results. While merging the partial results, the boundary between two partial results may be discontinuous. This discontinuity may occur as a result of two partial results being created from the edge vectors of different scanners.

Figure 5:
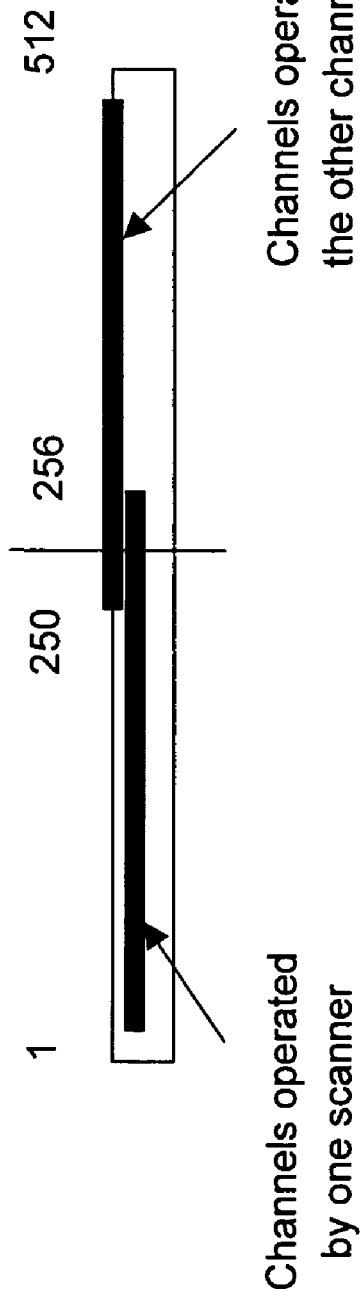
FIGS. 5 and 6 are diagrams illustrating a process for combining partial results in accordance with an exemplary embodiment of the invention.
Figure 6:
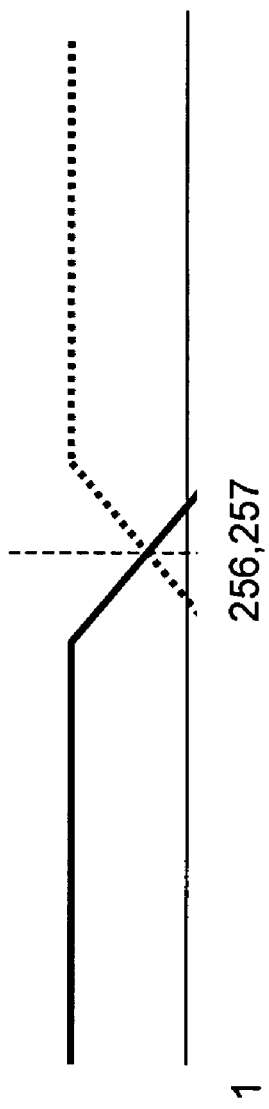

FIGS. 5 and 6 are diagrams illustrating a processing for combining partial results. In accordance with various embodiments of the invention, as shown in FIG. 5, a few center channels of the probe 202 (shown in FIG. 2) may be shared and controlled by more than one scanners 206 (shown in FIG. 2). As shown, one scanner 206 controls channels 1-256 and the other scanner 206 controls channels 250-506. However, each channel should be controlled by only one scanner 206 at any given time. Connector 204 (shown in FIG. 2) may include hardware protection to ensure that each channel is controlled by only one scanner 206 at a given time. In another embodiment, the overlapping channel data may be merged by taking an average over the region corresponding to the shared channels. In another embodiment of the invention, a transition weighting profile as shown in FIG. 6 may be used along a small region of overlap to merge the data. The overlap region corresponds to the boundaries of two partial results.

Figure 7:
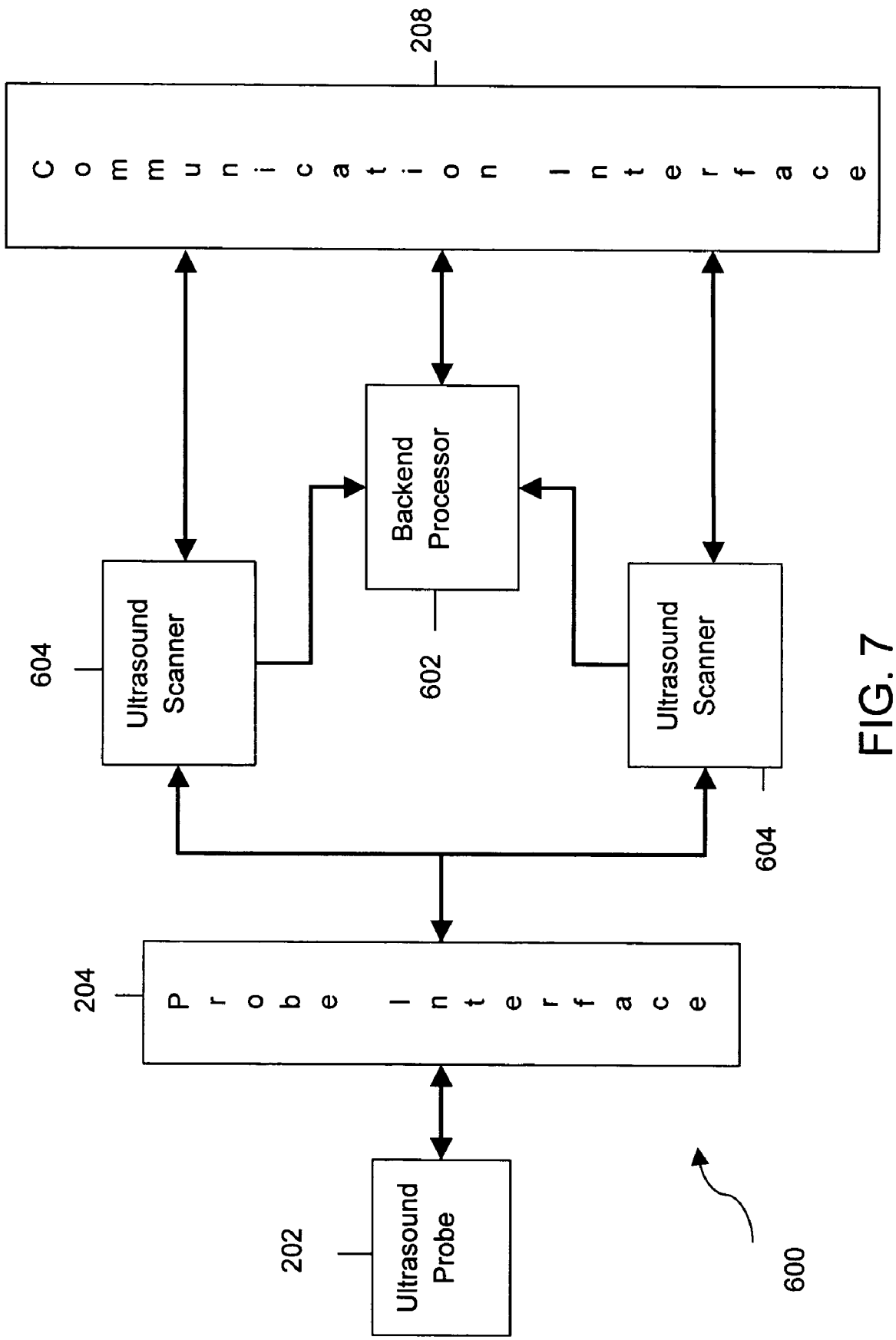
FIG. 7 is a block diagram of an ultrasound medical imaging system having a central backend processor in accordance with an exemplary embodiment of the invention.

In accordance with an embodiment of the invention, an ultrasound medical imaging system having a central backend processor is provided. FIG. 7 is a block diagram showing an ultrasound medical imaging system having a central backend processor.

The ultrasound medical imaging system 600 includes a high capacity dedicated computer or server standalone backend processor 602 with user inputs, such as, for example, a keyboard and controls. Standalone backend processor 602 has no frontend components such as transmit and receive boards. Standalone backend processor 602 may be configured as a master scanner controlling two standard ganged scanners 604. The backend resources may be implemented using grid computing.

Scanners 604 are in the slave mode. In various embodiments of the invention, more than two scanners 604 may be provided and configured in the slave mode, and which are ganged with standalone backend processor 602. Scanners 604 may include less hardware than a standard scanner. For example hardware such as monitors and keyboards may not be provided as part of scanners 604.

It should be noted that the various components and operations of the embodiments described herein may be modified as desired or needed. For example, propriety or standard interface 408 (shown in FIG. 4) may be a 10 Gig Ethernet (Xaui). 10 Gig Ethernet has four serial 3.125 GB/s data streams that are communicated on a physical link of an optical fiber. The 10 Gig Ethernet may communicate high volume data, such as a full backend IQ data of 120 MB/s. 10 Gig Ethernet may be used, for example, when ganging more than two scanners 206 (shown in FIG. 2) together.

Further, and for example, part of the processing, such as extrapolation may be performed by each ganged scanner 206. Accordingly, instead of transferring the scan converted data as partial results to the backend of the master scanner 206 or the backend process 602, partial image portions (e.g., processed data) may be transferred to the backend of the master scanner 206 as the backend processor 602. For example, if there are two scanners 206 with a 1024×768 pixel resolution display at 12-bit contrast depth, then about 1.5 MB uncompressed data will need to be transferred per frame, which is comparable to the previously described scan converted data rate of about 2 MB/s. The data to be transferred may be compressed using a hardware or software lossless compression.

The various embodiments of the invention may be used to reduce space requirements of the overall system by ganging notebook/laptop types of imaging devices.

The various embodiments of the invention provide a medical imaging system that performs complex image processing using, for example, multiple less expensive and less processing powered platforms. Modifications may be made to the scanners 206 as desired or needed, such as, for example, hardware changes such as modifying a data transfer scanner to a scanner high speed I/O interface.

A technical effect of embodiments of the invention is increased in speed of processing raw data (e.g., processing as real-time or post-processed data) in a medical imaging system by splitting raw data and processing it in parallel at each ganged scanner.

Another technical effect of some embodiments of the invention is increased flexibility of scanners. With increased computational resources processing algorithms of scanners such as, for example, EQ, B-mode, Color, Doppler processors, may be implemented in software instead of hardware. This provides easier reconfiguration such as rule based, learned and deterministic reconfiguration, as well as adaptable refinement of processing algorithms. For this purpose, a dedicated backend processor is used. The processing algorithms are implemented in software at this processor, facilitating the ease in reconfiguration and refinement.

While the invention has been described in terms of various specific embodiments, those skilled in the art will recognize that the invention can be practiced with modification within the spirit and scope of the claims.

What is claimed is:

1. An ultrasound system comprising:
a plurality of ultrasound scanners configured as a network;
a single ultrasound probe; and
a single connector for connecting the single ultrasound probe directly to the plurality of ultrasound scanners and configured to provide communication between the plurality of ultrasound scanners and the ultrasound probe, the single connector configured to split ultrasound data received from the ultrasound probe into a plurality of different data portions and transmit a different data portion directly to each of the plurality of ultrasound scanners, each ultrasound scanner configured to process the different data portion received from the single connector, and wherein each of the plurality of ultrasound scanners is configured to control at least part of a scan portion of the ultrasound probe.

2. An ultrasound system in accordance with claim 1 wherein the plurality of ultrasound scanners are configured to provide combined computing resources for use in connection with the ultrasound probe.

3. An ultrasound system in accordance with claim 1 wherein the single connector further comprises cables for connecting the plurality of ultrasound scanners in parallel, each of the cables having substantially the same length.

4. An ultrasound system in accordance with claim 1 wherein the plurality of ultrasound scanners are connected by at least one of (i) a wired connection and (ii) a wireless connection.

5. An ultrasound system in accordance with claim 1 wherein the plurality of ultrasound scanners are connected by one of an Ethernet connection and a high speed link.

6. An ultrasound system in accordance with claim 5 wherein the Ethernet connection is configured to communicate setup information and user input commands and the high speed link is configured to communicate synchronization information, image data and control parameters for controlling operation of the plurality of ultrasound scanners.

7. An ultrasound system in accordance with claim 5 wherein the high speed link is configured to have a transmission speed of at least 60 MB/s.

8. An ultrasound system in accordance with claim 1 wherein the plurality of ultrasound scanners are configured in a master-slave arrangement, with one ultrasound scanner configured as the master and at least one ultrasound scanner configured as the slave.

9. An ultrasound system in accordance with claim 8 wherein the master ultrasound scanner receives scan converted data from the at least one slave ultrasound scanner and is configured to process the received scan converted data to produce an image.

10. An ultrasound system in accordance with claim 9 wherein the scan converted data is communicated from the at least one slave ultrasound scanner to the master ultrasound scanner in a compressed format.

11. An ultrasound system in accordance with claim 8 wherein the master ultrasound scanner receives image data from the at least one slave ultrasound scanner and is configured to process the received image data to produce an image.

12. An ultrasound system in accordance with claim 1 wherein the parts of the scan portion of the ultrasound probe controlled by each of the plurality of ultrasound scanners is different.

13. An ultrasound system in accordance with claim 1 wherein a scan portion of the ultrasound probe is divided into logical sections each controlled by a different ultrasound scanner.

14. An ultrasound system in accordance with claim 1 further comprising a controller and wherein a number of ultrasound scanners needed to perform a scan using the ultrasound probe is automatically determined by the controller based upon the ultrasound probe connected to the plurality of scanners.

15. An ultrasound system in accordance with claim 1 wherein the ultrasound data comprises N channels of data transmitted from the ultrasound probe to the single connector, the single connector configured to transmit a first portion of the ultrasound data to a first ultrasound scanner and transmit a different second portion of the ultrasound data to a second ultrasound scanner that is coupled in parallel to the first ultrasound scanner, the first and second portions of ultrasound data each less than N channels.

16. A medical imaging system comprising:
a plurality of medical imaging devices coupled together in a parallel arrangement and configured to communicate therebetween;
a single medical examination device; and
a single connector for connecting the single medical examination device directly to the plurality of medical imaging devices, the single connector configured to provide communication between the plurality of medical imaging devices and the medical examination device, the single connector configured to split medical imaging data received from the medical examination device into a plurality of different data portions and transmit a different data portion directly to each of the plurality of medical imaging devices, each medical imaging device configured to process a different portion of the medical imaging data received from the single connector, and wherein each of the plurality of medical imaging devices is configured to control at least part of a scan portion of the single medical examination device.

17. A medical imaging system in accordance with claim 16 wherein the medical imaging devices comprise ultrasound scanners and the medical examination device comprises an ultrasound probe.

18. A medical imaging system in accordance with claim 16 wherein the medical imaging devices are configured in a master-slave arrangement to control the medical examination device.

19. An ultrasound system comprising:
a plurality of ultrasound scanners;
a single ultrasound probe;
first means for connecting the plurality of ultrasound scanners in parallel to provide communication between the plurality of ultrasound scanners; and
second means for connecting the single ultrasound probe directly to the plurality of ultrasound scanners and splitting medical imaging data received from the ultrasound probe into a plurality of different data portions and transmitting a different data portion directly to each of the ultrasound scanners such that each of the plurality of ultrasound scanners processes the different portion, and wherein each of the plurality of ultrasound scanners is configured to control at least part of a scan portion of the single ultrasound probe.

20. A method for controlling operation of an ultrasound probe, the method comprising:
configuring a plurality of ultrasound scanners to operate in parallel and for communication therebetween to control a single ultrasound probe that is coupled directly to the plurality of ultrasound scanners via a single connector;
controlling operation of at least part of a scan portion of the ultrasound probe with each of the ultrasound scanners;
splitting ultrasound data received from the ultrasound probe into a plurality of different data portions;
transmitting a different data portion directly to each ultrasound scanner; and
processing the different portions of ultrasound data from the ultrasound probe using different ones of the plurality of ultrasound scanners.

21. A method in accordance with claim 20 further comprising configuring the plurality of ultrasound scanners in a master-slave arrangement.

* * * * *